United States Patent
Branemark

[11] Patent Number: 5,360,449
[45] Date of Patent: Nov. 1, 1994

[54] ARTIFICIAL JOINT MECHANISM FOR RECONSTRUCTING HUMAN JOINTS

[75] Inventor: Per-Ingvar Brånemark, Mölndal, Sweden

[73] Assignee: Medevelop AB, Sweden

[21] Appl. No.: 940,961

[22] PCT Filed: Sep. 5, 1991

[86] PCT No.: PCT/SE91/00586
§ 371 Date: Nov. 5, 1992
§ 102(e) Date: Nov. 5, 1992

[87] PCT Pub. No.: WO92/03992
PCT Pub. Date: Mar. 19, 1992

[30] Foreign Application Priority Data
Sep. 5, 1990 [SE] Sweden .................... 9002823

[51] Int. Cl.5 .................... A61F 2/32; A61F 2/42
[52] U.S. Cl. .................... 623/18; 623/21
[58] Field of Search .............. 623/18, 19, 20, 21

[56] References Cited
U.S. PATENT DOCUMENTS

| | | | |
|---|---|---|---|
| 3,991,425 | 11/1976 | Martin et al. | 623/21 |
| 4,216,549 | 8/1980 | Hillberry et al. | 623/20 |
| 4,301,553 | 11/1981 | Noiles | 623/20 |
| 4,383,337 | 5/1983 | Volz et al. | 623/18 |
| 4,714,473 | 12/1987 | Bloebaum | 623/20 |
| 4,784,661 | 11/1988 | Beckenbaugh et al. | 623/21 |
| 4,944,758 | 7/1990 | Bekki et al. | 623/21 |
| 5,007,933 | 4/1991 | Sidelootham et al. | 623/20 |
| 5,152,794 | 10/1992 | Dividson | 623/20 |

Primary Examiner—David Isabella
Attorney, Agent, or Firm—Ostrolenk, Faber, Gerg & Soffen

[57] ABSTRACT

An artificial joint mechanism for use in reconstructing joints such as wrists and finger joints. The joint mechanism is designed for use between fixtures anchored in the bone and/or tissue on each side of the joint. The joint mechanism comprises a male part (1) with at least one joint pin protruding from a base plate (4) and having a substantially arc-shaped joint surface, and a female part (2) with a recess (13) corresponding to the joint pin and having a substantially arc-shaped defining surface (14) for contact with said joint surface in the male part.

8 Claims, 3 Drawing Sheets

ARTIFICIAL JOINT MECHANISM FOR RECONSTRUCTING HUMAN JOINTS

FIELD OF THE INVENTION

The present invention relates to an artificial joint mechanism for use in reconstructing joints such as wrists, finger joints, etc., and is designed for use between fixtures anchored in the bone and/or tissue on each side of the joint.

BACKGROUND OF THE INVENTION

Previously known joint mechanisms for finger joints and wrists, for instance, generally comprise a pad of resilient material which has been secured in suitable manner between fixtures anchored in the bone and/or tissue on each side of the natural joint which has been removed—see for instance U.S. Pat. application Ser. No. 406,586 filed Sep. 13, 1989 by Per-Ingvar Branemark and issued on Nov. 5, 1991 as U.S. Pat. No. 5,062,851 entitled Anchoring Element For Supporting a Joint Mechanism of a Finer or Other Reconstructed Joint.

However, in practice such a resilient pad has proved to have certain limitations both as to general strength and also since it lacks certain joint functions—controllable bending, lateral movement, particularly in the case of wrists, effective "locking" when under load, e.g. when the palm of the hand is used as support, etc.

SUMMARY OF THE INVENTION

The object of the invention is to eliminate the above-mentioned difficulties and drawbacks in the type of artificial joint mechanisms described above and to achieve a joint mechanism which is simple in design but still permits stable bending positions and lateral movement, and is also vastly superior to previously known constructions from the point of view of wear.

This is solved according to the invention primarily in that it comprises a male part with at least one joint pin protruding from a base plate and having a substantially arc-shaped joint surface, like a sector of a cylinder, and a female part with a recess corresponding to the joint pin and having a substantially arc-shaped defining surface, like a sector of a cylinder, for contact with said joint surface in the male part.

According to a preferred embodiment of the invention the joint surface of the male part comprises two part surfaces separated by a central recess, said part surfaces being aligned with each other along the centre line of the base plate and extending from said recess towards the short sides of the base plate.

Suitably each part joint surface is provided with a first joint portion located close to the recess, running substantially parallel to the base plate and then continuing into a second joint portion running with slightly downward inclination towards the short sides of the base plate.

The first part joint surfaces in the male part thus cooperate with the recess in the female part, acting as a joint at bending movements, while the desired lateral movement is achieved by cooperation of the second, inclined joint portions in the male part with the recess in the female part.

According to another embodiment of the invention-the second joint portions of the part join surfaces may, depending on anatomical criteria, have different angles of inclination ($\alpha$ and $\beta$) in relation to the base plate.

The angles of inclination between the base plate and the second joint portions may suitably lie between 0° and 50°. The joint portions are arc-shaped and suitably define a sector angle of between 10° and 350°.

According to yet another embodiment of the invention the second joint portions of the male part may have a different, optional profile, and be arranged to cooperate with differently profiled recesses in the female part.

According to the invention the male part and the female part are secured against displacement along their cooperating surfaces. This is suitably achieved by means of bosses protruding from the joint surfaces or contact surfaces of the male and/or female parts and arranged to cooperate with corresponding recesses in respective parts or by the lateral ends of either the male or the female part being arranged to grip the short ends of the male or female part.

According to another embodiment of the invention the actual bending movement may suitably be limited by one edge portion of the female part being arranged to be brought into contact with one of the side surfaces of the base plate of the male part.

The joint mechanism according to the invention suitably consists of a biocompatible material and according to a preferred embodiment the male part consists of titanium and the female part of a suitable plastic material.

BRIEF DESCRIPTION OF THE DRAWINGS

The invention will be described in more detail in the following descriptions with reference to an embodiment illustrated in the accompanying drawings in which.

DETAILED DESCRIPTION OF DRAWING

Figure 1:
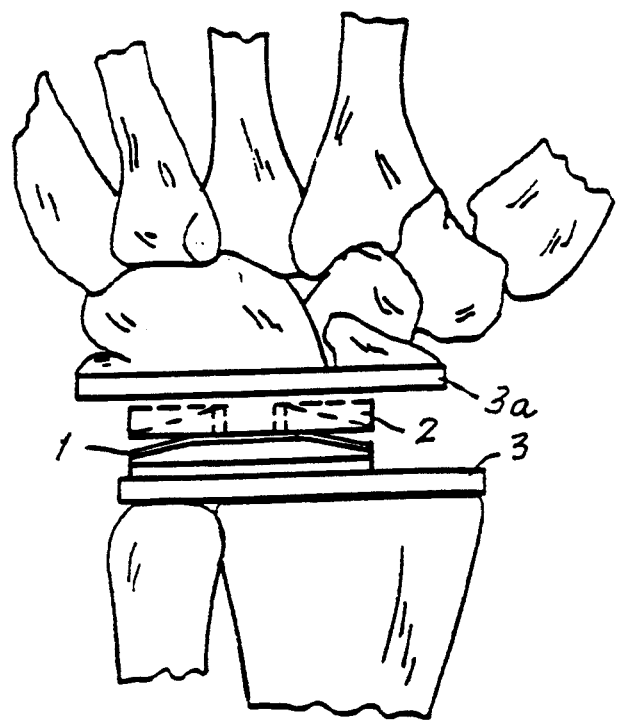
FIG. 1 shows in a first preferred embodiment the construction of a hand with a normal wrist with the joint mechanism according to the invention applied.
Figure 3:
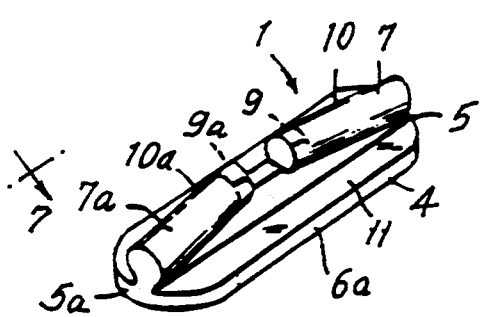
FIGS. 2 and 3 are views in perspective showing the lower and upper side of the male joint component part of the joint mechanism of the first preferred embodiment.
Figure 2:
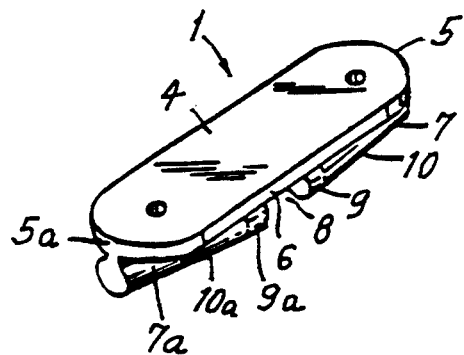

The joint mechanism proposed according to the invention and illustrated in a first preferred embodiment in the drawings (FIG. 1 to FIG. 6) comprises in principle a male joint component and a female joint component 2 cooperating therewith. The male joint component 1 also shows in principle a protruding joint surface designed to cooperate with a corresponding recess in the female component 2. The two components 1, 2 are detachably secured on the sides not cooperating with each other, to fixtures 3, 3a, not shown in detail, which have been implanted in the bone and/or tissue with the aid of bone and/or tissue anchoring devices after surgical removal of the natural joint.

Figure 8:
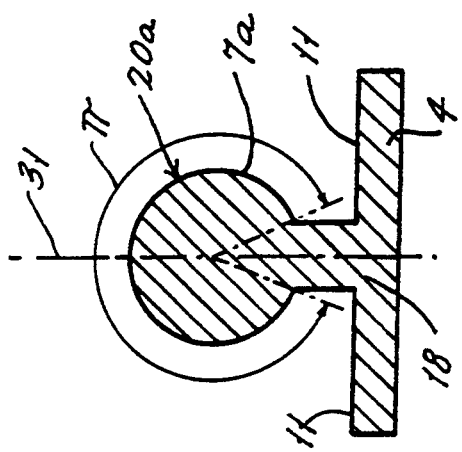
FIG. 8 is a cross-section taken through line 8—8 of FIG. 7 looking in the direction of arrows 8—8.

In the first preferred embodiment shown on the drawings the male component 1 comprises a substantially rectangular base plate 4 with opposite short sides 5, 5a and opposite long sides 6, 6a. The joint surface of the male part 1 consists of two joint pins 20, 20a are aligned with each other, extending along the centre line of the base plate 4 and lying in plane 31 (FIG. 8) that is perpendicular to base plate surface 11. Aligned joint surface parts 7, 7a of respective pins 20, 20a extend from a central recess 8 between joint pins 20, 20a towards the short sides 5, 5a of the base plate 4.

Each of the joint surface parts 7, 7a includes relatively short a first joint portion 9, 9a located close to the central recess 8, running substantially parallel to the base plate 4 and continuing into a relatively long second joint portions 10, 10a, respectively, which runs with slightly downward inclination towards the short sides 5, 5a of the base plate surface 11. A support formed by vane 18 which is disposed in plane 31 (FIG. 8) that is perpendicular to base surface 11.

Figure 7:
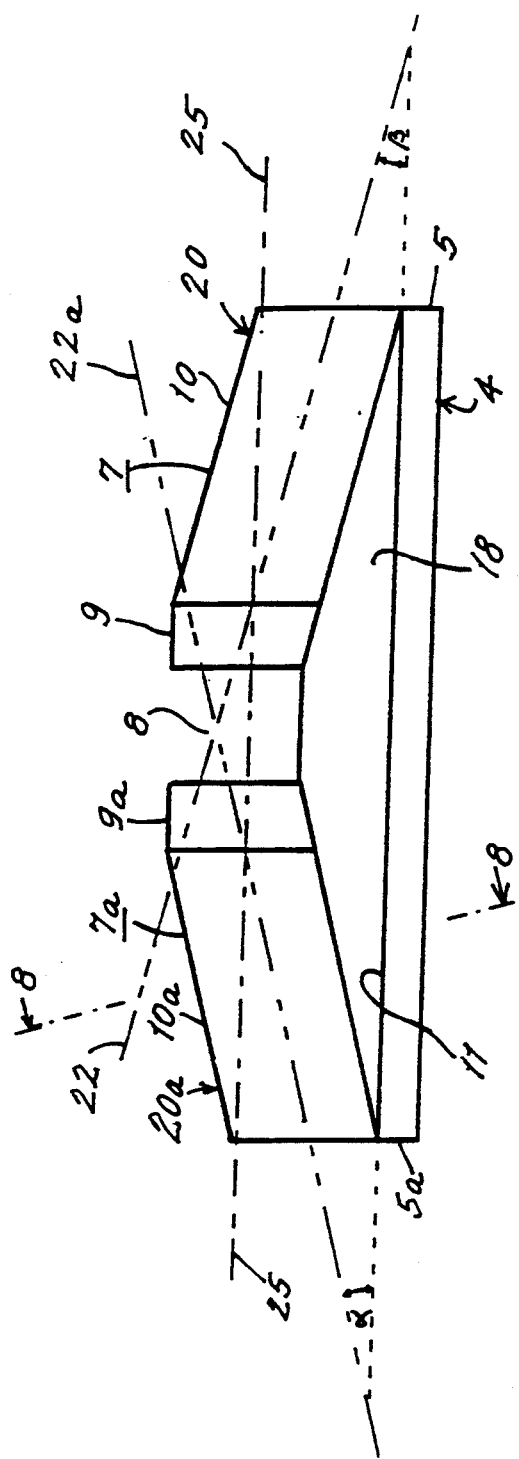
FIG. 7 is an enlarged side elevation of the male joint component looking in the direction of arrows 7—7 in FIG. 3.

The angles of inclination $\alpha$ and $\beta$ may vary depending on the anatomical criteria. Angle $\alpha$ (FIG. 7) is included between base surface 11 and longitudinal axis 22a of longer pin portion 10a, and angle $\beta$ is included between base surface 11 and longitudinal axis 22 of longer pin portion 10.

The angles of inclination $\alpha$ and $\beta$ may be as much as 50°, preferably about 10°. Line 25 (FIG. 7) is parallel to base surface 11 and indicates generally the location for the axis of short pin portions 9, 9a.

All the joint surface portions 9, 9a; 10, 10a are arc-shaped, like a sector of a cylinder, each joint surface suitably defining a sector angle 90 of between about 10 to 350°, preferably 40° to 320°.

The side edges of the base plate 4 located outside of vane 18 that support pins 20, 20a.

Figure 4:
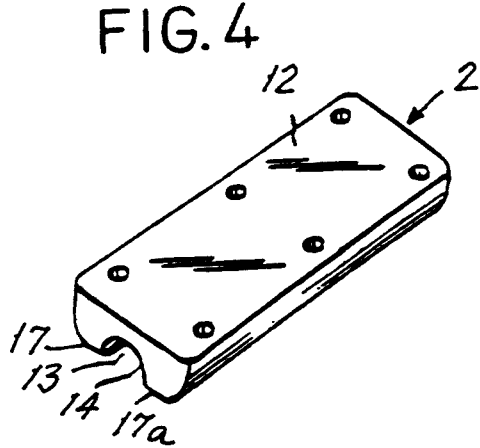
FIG. 4 is an end view of the female joint component included in the proposed joint mechanism of the first preferred embodiment.
Figure 5:
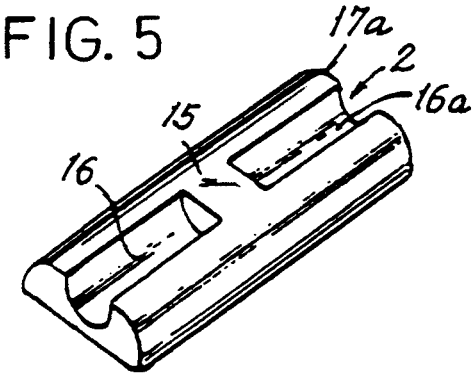
FIG. 5 shows the female joint component seen from below of the first preferred embodiment.
Figure 6:
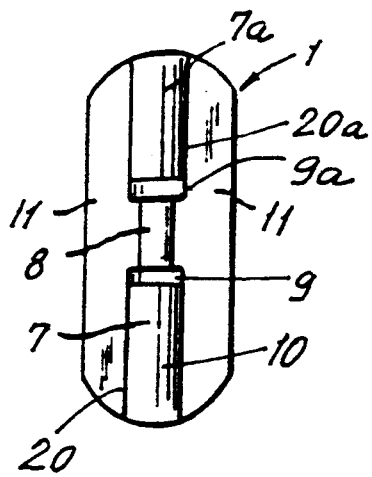
FIG. 6 shows the male joint component of the first preferred embodiment illustrated in FIG. 3, seen from above.

As shown in more detail in FIGS. 4 and 5, the female joint component 2 also consists of substantially rectangular base plate 12 with a longitudinal central recess 13 having arc-shaped defining surface 14. A protruding shoulder 15 is provided centrally in the recess 13 and is intended to extends into and cooperate with the central recess 8 in the male component 1. Two contact surfaces 16, 16a are thus also formed on each side of the shoulder 15, intended to cooperate with the arc-shaped joint surfaces 7, 7a of the male component. The female component 2 is also provided with substantially flat defining surfaces 17, 17a—one on each side of the recess 13 and confronting surface 11 when components 1 and 2 are operatively engaged.

When components 1, 2 are fitted together the joint mechanism shown offers the following important functions:

achievement of a stable normal bending function of the joint, where the contact surfaces 16, 6a partially—i.e. with the portions located close to the guide shoulder 15—cooperate with the first joint portions 9, 9a of the male component, achievement of a limitation of the bending movement controllable in advance, in that the defining surfaces 17, 17a are brought into contact with the side surfaces 11 of the base plate 4 in the male component 1, achievement of bending to a secured position, since the guide shoulder 15 of the female component engages in the central recess 8 of the male part 1, thus preventing lateral displacement of either component, 1 or 2 achievement of lateral bending movement since the contact surfaces 16, 16a are brought into contact with the inclined second or longer pin portions 10, 10a of the male component 1, and achievement of a stable support joint if, for instance, strong pressure is exerted on the mechanism by the palm of the hand when the body is raised from a sitting position, for instance.

The male and female components are manufactured from material compatible with tissue. According to a preferred embodiment one part, suitably the male component is made of metal, suitably titanium, and the female component of a plastic material, suitably polyethylene. Different materials are preferably used in the two parts in order to reduce wear.

Variations in the joint mechanism described are of course possible within the scope of the following claims. If for some reason no lateral bending movement is necessary, the second longer joint pins 10, 10a need not be inclined but are aligned with the first joint parts 9, 9a.

Furthermore, the risk of lateral displacement of the two components 1, 2 can be avoided by designing the short sides of the female part to grip the short sides of the male part, for instance, or the short sides of the joint member, in which case the shoulder 15 and recess 8 can be omitted. Furthermore, more than one shown locking arrangement may be provided between shoulder and recess. As to the design of the concentric joint surfaces of the male and female parts which cooperate with each other, instead of being arc-shaped, suitably circle-arc shaped, these could also have different surface profiles of suitable design. The first and second joint surfaces may also have different profiles from the first joint surfaces.

Figure 9:
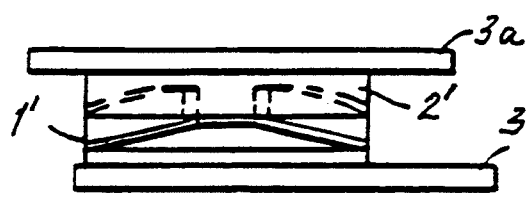
FIG. 9 shows a second preferred embodiment of the invention in a representation corresponding to that in FIG. 1.
Figure 10:
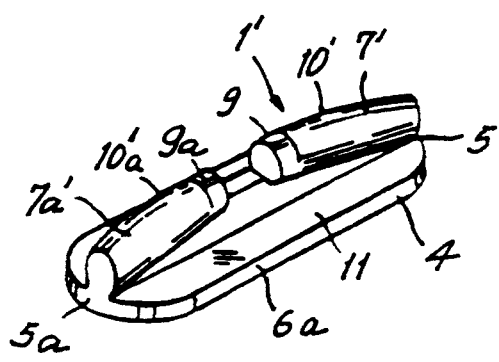
FIG. 10 shows the second preferred embodiment of the invention in a representation corresponding to that in FIG. 3.
Figure 11:
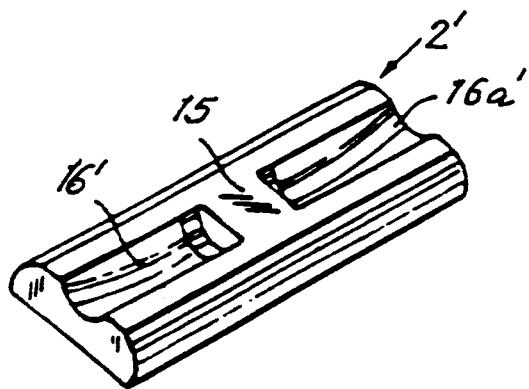
FIG. 11 shows the second preferred embodiment of the invention in a representation corresponding to that in FIG. 5o

The joint mechanism according to a second preferred embodiment of the invention is shown in FIGS. 9 to 11. It comprises a male part 1' and a female part 2' cooperating substantially in the same way as, in the first preferred embodiment, the male component 1 is cooperating with the female component 2, except that the second joint portions 10', 10a' of the two-part joint surfaces 7', 7'a of pins 10, 10a but not their first joint portions 9' and 9' located close to the central recess 8' are substantially banana-shaped. The second joint portions 10' and 10a' run parallel to the long side 6a and inclined slightly towards the short sides 5 and 5a of the unchanged base plate 4.

The female component 2' of the second preferred embodiment is designed to fit the male component 1' by i being provided with recesses having substantially negatively banana-shaped surfaces 16' and 16'a, the recesses being arranged on either side of a protruding shoulder 15.

The two component joint surfaces 7', 7'a of the male part of the second preferred embodiment are aligned with each other, and are running with slightly downward inclination towards the short sides 5 and 5a of the base plate. Their angles of inclination $\alpha'$ and $\beta'$, not indicated in the Figures but essentially similar to angles $\alpha$ and $\beta$ of the first preferred embodiment and variable within the same limits, i.e. between 0° and 50°, preferably being about 10°, may vary depending on anatomical criteria.

All the joint surface portions 9, 9a,; 10'10'a of the male part of the second preferred embodiment are arc-shaped, each joint surface defining a sector angle of between 10° to 350°, preferably 40 to 320°.

While the second preferred embodiment is equally efficient in its "locking" action, it surpasses the first preferred embodiment especially with regard to ease of lateral movement.

I claim:

1. An artificial joint mechanism for reconstruction of joints intended for mounting between fixtures anchored on each side of the joint, said artificial joint mechanism comprising:

a male joint component comprising a first base plate and first and second joint pins attached to one surface of said first base plate by means of a support element interspaced between each of said joint pins and said first base plate, said joint pins being separated by a central recess, each of said joint pins being provided with a substantially cylindrical arc-shaped first joint surface formed about an individual first axis both of said first axes being located in a first plane disposed generally perpendicular to said one surface of said first base plate;

a female joint component comprising a second base plate provided on one side thereof with first and second joint recesses separated by a shoulder, each of said joint recesses having an individual substantially cylindrical arc-shaped second joint surface formed about an individual second axis, both of said second axes being located in a second plane disposed generally perpendicular to said second base plate;

said first and second joint pins being disposed within said first and second joint recesses, respectively, and said second joint surfaces being engaged with said first joint surfaces for cooperation with each other during relative movement between said male and female joint components;

each of said first and second joint pins being provided with an arc-shaped first joint portion located adjacent to and extending from said central recess, each of said first joint portions being relatively short compared to each of said first joint surfaces, each of said arc-shaped first joint portions having a third axis arranged generally parallel to said one surface of said first base plate;

each of said first axes being inclined slightly with respect to said one surface of said first base plate, and said first axes being inclined with respect to one another.

2. The joint mechanism of claim 1, wherein each of said first axes is disposed at a different angle of inclination with respect to said one surface of said first base plate.

3. The joint mechanism of claim 1, wherein said angles of inclination are no greater than 50°.

4. The joint mechanism of 1, wherein said angles of inclination are about 10°.

5. The joint mechanism of claim 1, wherein each of said arc-shaped first joint surfaces covers a sector having an angle in a range of between 10° and 350°; said sector being located in a plane perpendicular to said first axis about which the respective first joint surface is formed.

6. The joint mechanism of claim 1, wherein each of said arc-shaped first joint surfaces covers a sector having an angle in a range of between 40° and 320°; said sector being located in a plane perpendicular to said first axis about which the respective first joint surface is formed.

7. The joint mechanism of claim 1, wherein each of said first joint surfaces defines a first profile and each of said first joint portions has a second profile that is different than said first profile, and each of said second joint surfaces is operatively engaged with an individual one of said joint pins at its said first and second profiles.

8. The joint mechanism of claim 7, wherein the profiles of said first joint surfaces are substantially of crescent shape.

* * * * *